United States Patent
Pearson (10) Patent No.: US 9,629,540 B2
(45) Date of Patent: Apr. 25, 2017

(54) TEAR DUCT RESISTANCE MEASURING SYSTEM

(71) Applicant: LJT PROJECTS LIMITED, Maidenhead (GB)

(72) Inventor: Andrew Robert Pearson, Reading (GB)

(73) Assignee: LJT PROJECTS LIMITED, Berkshire (GB)

( * ) Notice: Subject to any disclaimer, the term of this patent is extended or adjusted under 35 U.S.C. 154(b) by 179 days.

(21) Appl. No.: 14/362,306

(22) PCT Filed: Nov. 30, 2012

(86) PCT No.: PCT/GB2012/052964
§ 371 (c)(1),
(2) Date: Jun. 2, 2014

(87) PCT Pub. No.: WO2013/079959
PCT Pub. Date: Jun. 6, 2013

(65) Prior Publication Data
US 2014/0358039 A1    Dec. 4, 2014

(30) Foreign Application Priority Data

Dec. 2, 2011    (GB) .................................. 1120771.9

(51) Int. Cl.
*A61B 5/103*    (2006.01)
*A61B 5/117*    (2016.01)
(Continued)

(52) U.S. Cl.
CPC ................ *A61B 3/101* (2013.01); *A61B 3/10* (2013.01); *A61B 5/036* (2013.01); *A61B 5/6821* (2013.01);
(Continued)

(58) Field of Classification Search
CPC ........... A61B 3/10; A61B 3/101; A61B 5/036; A61B 5/6821; A61B 2010/0067; A61F 9/00772; A61F 9/00736
See application file for complete search history.

(56) References Cited

U.S. PATENT DOCUMENTS 4,670,006 A * 6/1987 Sinnett ................ A61F 9/00736
604/119
4,891,044 A * 1/1990 Mitchell ............. A61F 9/00736
604/27
(Continued)

FOREIGN PATENT DOCUMENTS

| WO | 02/17833 A1 | 3/2002 |
|---|---|---|
| WO | 2009/111726 A2 | 9/2009 |
| WO | 2012/037428 A2 | 3/2012 |

OTHER PUBLICATIONS

International Search Report for International Application No. PCT/GB2012/052964, dated Mar. 5, 2013.
(Continued)

*Primary Examiner* — Devin Henson
(74) *Attorney, Agent, or Firm* — Heslin Rothenberg Farley & Mesiti P.C.; Victor A. Cardona, Esq.

(57) ABSTRACT

A system for measuring the flow properties of a tear duct, to ascertain its flow resistance, includes a syringe communicating with a cannula to supply liquid to a punctum of an eye, the cannula having a tip to seal to the punctum. A motor is arranged to actuate the syringe. A pressure sensor monitors the pressure of the liquid supplied to the punctum. A monitoring circuit provides an indication of the flow resistance. A feedback circuit controls the motor in accordance with the measured pressure, to maintain a preset liquid pressure, or to ensure that the liquid pressure does not exceed a preset threshold. The system may prevent flow through the other punctum of the eye. If the flow rate of the
(Continued)

liquid supplied to the punctum is also monitored, the monitoring circuit is arranged to determine the flow resistance from the pressure and the flow rate.

34 Claims, 3 Drawing Sheets

(51) Int. Cl.
    *A61B 3/10*     (2006.01)
    *A61B 5/00*     (2006.01)
    *A61B 10/00*     (2006.01)
    *A61B 5/03*     (2006.01)
    *A61F 9/007*     (2006.01)

(52) U.S. Cl.
    CPC ... *A61B 2010/0067* (2013.01); *A61F 9/00736* (2013.01); *A61F 9/00772* (2013.01)

(56) References Cited

U.S. PATENT DOCUMENTS

| | | | | |
|---|---|---|---|---|
| 5,832,930 | A * | 11/1998 | Martin | A61B 17/1227 128/898 |
| 7,998,497 | B2 * | 8/2011 | de Juan, Jr. | A61F 9/0017 424/423 |
| 8,460,230 | B2 * | 6/2013 | Perry | A61B 3/16 604/19 |
| 2004/0171983 | A1 * | 9/2004 | Sparks | A61M 5/16827 604/65 |
| 2005/0038323 | A1 * | 2/2005 | Valazzi | A61B 1/015 600/153 |
| 2005/0054971 | A1 * | 3/2005 | Steen | A61F 9/00736 604/22 |
| 2010/0145302 | A1 | 6/2010 | Cull et al. | |
| 2010/0324476 | A1 | 12/2010 | Boukhny et al. | |
| 2011/0060229 | A1 * | 3/2011 | Hulvershorn | A61B 5/0215 600/486 |
| 2011/0071481 | A1 * | 3/2011 | Chen | A61B 17/12 604/290 |

OTHER PUBLICATIONS

Written Opinion of the International Search Authority for International Application No. PCT/GB2012/052964, dated May 14, 2013.
UK Search Report Under Section 17 for International Application No. GB1120771.9 dated Mar. 23, 2012.
Opthalmology, West Virginia University School of Medicine, Morgantown, WV; vol. 102(11), 1995, Tucker, Measurement of the resistance to fluid flow within the lacrimal outflow system, pp. 1639-1645.
Journal of Clinical Engineering, West Virginia University; Morgantown, WV; vol. 16, 1991, Stanley, Instrument to test patency of lacrimal drainage system, 57-60.

* cited by examiner

TEAR DUCT RESISTANCE MEASURING SYSTEM

CROSS REFERENCE TO RELATED APPLICATIONS

This application is a national stage filing under section 371 of International Application No. PCT/GB2012/052964, filed on Nov. 30, 2012, and published in English on Jun. 6, 2013, as WO 2013/079959 and claims the priority of GB application No. 1120771.9 filed on Dec. 2, 2011, the entire disclosure of these applications being hereby incorporated herein by reference.

The present invention relates to a system and to a method for measuring the flow properties of a tear duct, to ascertain the flow resistance of the tear duct.

BACKGROUND

Watering from the eyes due to narrowing or occlusion of the tear ducts, that is to say the tear drainage ducts, is a common problem. In a healthy individual the tear drainage system collects the tears from the inner corner of the eye through a small opening (punctum) in the margin of the eyelid, there being one punctum in each of the upper and lower eyelids. Each punctum leads to a canaliculus which passes horizontally through the medial end of the eyelid towards the nose, the canaliculi usually joining to form a single common canaliculus as they reach the lacrimal sac. Here the tear duct changes to an inferior direction passing downward to become the lacrimal duct and finally exiting into the lower part of the nose.

Narrowing or occlusion of the tear duct can occur at any point in its course from the eye to nose. Typically, the evolution of tear duct obstruction involves a progressive narrowing of the tear duct from an initially fully open state, through in some cases to complete occlusion. The consequent reduction in tear drainage leads to troublesome watering from the eye, soreness of the eyelids, and sometimes infections.

Well-established techniques of tear duct surgery are available to improve drainage. Surgery is usually of value where complete obstruction exists and is often indicated before the system is completely obstructed as troublesome watering can still be corrected. It is known that many patients with eye watering do not have completely occluded tear systems. In these cases it can often be difficult to ensure that the tear duct is the cause of watering from the eye, to monitor the process of narrowing, to decide when to intervene, and to assess the response to treatment. In general, the greater the degree of narrowing the higher is the likelihood of a successful outcome from surgery. A test that could accurately measure the degree of narrowing in a simple and safe way would be very useful.

Several clinical tests can be used to help decide how narrow the tear duct is. For example, basic information can be derived by examining the tear film height and estimating the speed of clearance of a drop of fluorescein colouring in the tear film. Jones tests, which rely on identifying passage of fluorescein to the nose, have been advocated for assessing watering where the tear system is at least partly open, but are known to have high levels of inaccuracy. Radiological tests looking at the anatomy and physiological function of the tear system are also known, but can be expensive and time-consuming, and are subjective and prone to errors of administration or interpretation.

In practice the mainstay of clinical examination is to use a lacrimal cannula inserted into the punctum and connected to a syringe to irrigate fluid down the tear system. The syringe and cannula are hand-held, fluid is irrigated under pressure and the passage of fluid to the nose or regurgitation back from the same or, because they are connected, the opposite punctum, is identified. With experience a subjective estimate can be made of the level of resistance to fluid flow.

Tucker et al (Ophthalmology, Vol. 102, No. 11 (November 1995) p. 1639) has described a more objective measure of lacrimal resistance, where resistance=pressure/flow. By sealing an irrigating cannula tip at the punctum, irrigating with water at a known flow rate, and recording the pressure generated, figures for resistance were derived in normal subjects and those with open tear ducts following successful lacrimal surgery. However the research equipment used has a number of drawbacks which would prevent application in a clinical environment and use in those where tear duct narrowing or occlusion is present, as is usually the case.

SUMMARY OF THE INVENTION

Accordingly the present invention provides a system for measuring the flow properties of a tear duct, to ascertain the flow resistance of the tear duct, the system comprising:

a means to generate a flow of liquid, communicating with a cannula to supply liquid to a punctum of an eye, the cannula defining a tip and being able to seal to the punctum;

a motor to actuate the flow-generating means;

a pressure sensor to monitor the pressure of the liquid supplied to the punctum;

a monitoring circuit to which signals from the pressure sensor are provided, arranged to provide an indication of the flow resistance from those signals; and a feedback circuit to control the motor in accordance with signals from the pressure sensor, either to maintain a preset liquid pressure, or to ensure that the liquid pressure does not exceed a preset threshold.

The system may be portable, or may be mounted on a microscope, or indeed may be usable in either way. The system may be battery-powered. Preferably the system also includes means to close the other punctum of the eye, for example a clip or a plug. The closure means ensure that the liquid introduced into the punctum must flow through the tear duct. Without such a closure means, leakage of injected liquid might otherwise occur through the other punctum, giving misleadingly low values for fluid pressure. If the tear duct is completely obstructed there can be no through flow, and the feedback circuit ensures the liquid pressure does not exceed the preset threshold. This ensures the patient is not subjected to pain or damage to the tear duct, as could otherwise occur.

Thus for safely and accurately testing the tear duct where narrowing or occlusion are suspected the system provides feedback control of the irrigation and ensures that the lacrimal system is closed apart from the nasal exit point of the tear duct. Further features ensure that the system is practical for clinical use.

In one embodiment the flow-generating means is a syringe. The motor is arranged to actuate the syringe.

In some cases it may be realistic to assume the flow rate has a predetermined value, for example as determined by the voltage applied to a motor. Hence, for a predetermined voltage, the monitored pressure is indicative of the flow resistance of the tear duct, and may be used as a parameter representing the flow resistance. However, more accurate measurements may be obtained if the flow rate is also monitored, as this will enable the flow resistance to be calculated, as explained below. Hence the system may also comprise means to monitor the flow rate of the liquid supplied to the punctum. Signals from the flow rate monitor may then be supplied to the monitoring circuit.

The system is capable of irrigating the tear duct, while monitoring both the pressure applied and the flow rate through the lacrimal system. By eliminating leakage except at the nasal end of the tear duct the lacrimal system acts as a closed conduit such that, with pressure (P) and flow (F) both known, resistance (R) can be calculated as R=P/F. The system uses a syringe driver so that the rate of flow of the liquid is controlled electronically in response to continuous pressure recordings from a pressure transducer in the fluid delivery system to the tear duct. A certain motor speed on the syringe driver will propel the plunger of the syringe at a known linear rate from which the rate of delivery of fluid from any particular size or type of syringe can be ascertained. The flow rate may therefore be monitored by monitoring the movement of the syringe plunger, or by monitoring the motor which drives the syringe plunger. Alternatively the liquid flow may be directly monitored. (As mentioned above, in some cases the liquid flow rate need not be monitored.)

The syringe communicates with the cannula either directly, or through one or more components that define a flow path, for example through a flexible tube. The pressure sensor may be within the syringe, or within another part of the flow path, in order to monitor the pressure of the liquid supplied to the punctum. In one embodiment the flow path is defined in part by a short tubular element to which the cannula is attached, and this short tubular element is preferably rigid. The short tubular element may be less than 150 mm long, more preferably less than 100 mm long, but preferably at least 5 mm long, and more preferably at least 20 mm long; it therefore provides a convenient way for the operator to manipulate the cannula, for example with his fingertips. The cannula may be readily detachable from the short tubular element, so it can be replaced by a cannula of a different shape or size. Alternatively the cannula may be integral with the short tubular element. The short tubular element may include means to activate the system, such as a touch-sensitive switch. As a preferred option, the pressure sensor is within the short tubular element, which may be referred to as a transducer module.

In a second aspect, the invention therefore provides a tubular element which may be used in such a flow resistance measuring system, the tubular element being adapted to communicate at one end with a cannula to supply liquid to a punctum of an eye, the cannula defining a tip and being able to seal to the punctum, and the tubular element being adapted to communicate at the other end with a source of liquid; the tubular element being adapted to be handheld; the tubular element comprising a pressure sensor to monitor the pressure of the liquid supplied to the punctum; and comprising a switch to activate the liquid supply source.

Measurements are preferably only made when the pressure and flow rate are stable, if only for a few seconds, as measurements made in a non-steady-state condition may give inaccurate results. With two variables it would be possible to keep either one constant and measure the other. Thus if there is a constant rate of flow the pressure could be recorded, and the system is arranged to reduce or cut off the flow if the pressure becomes excessive. A preferred alternative is to specify the preset pressure at which the system will irrigate the tear duct and to vary the speed of the syringe driver, and so the flow rate, to provide this. This is closer to the natural physiological process of tear drainage, especially if the selected pressure is relatively low; and it avoids the risk of leakage, pain for the patient, or damage to the tear duct or syringe driver system that may occur if the irrigation pressure were allowed to rise to a high level.

A substantial advantage of the system arises where it is portable, so it can be used hand-held, but where it can also be mounted on the slit-lamp biomicroscope used for eye examination. Irrigating the tear ducts with the patient seated at the microscope is currently very difficult in view of the limited space available to work in. A further problem is the necessarily long length of a filled syringe attached to a currently-available lacrimal irrigating cannula. Such length makes positioning the tip of the cannula in the punctum and applying pressure to the syringe very awkward and there is potential for damage to the tear duct, eyelid or eye. Typically, syringing of the tear duct therefore takes place away from the microscope, often requiring transfer to a couch.

There are clear advantages in being able to perform this test at the microscope. Not only is it simpler in not requiring the patient to be moved, but also the illumination and magnification provided by the microscope allow ready visualisation of the punctum, simple placement of the tip of the cannula in to the required position and the ability to check for leaks when irrigation commences as well as accurate placement of the closure means on the opposite punctum. The system of the invention allows for testing at the microscope by incorporating a number of features. The syringe driver is portable and of a compact size. It is designed to fit within the limited available space on the microscope, and to be removably mounted on the base plate of the microscope used for other ophthalmic work. A length of flexible tubing connects the tip of the syringe to the short tubular element, to which is attached a short cannula. The combination of the short tubular element and the cannula is sufficiently compact to allow ready manipulation in the narrow confines of the microscope and simple placement of the cannula. Achieving this however requires the use of both of the operator's hands, one to hold the eyelid stable, the other to hold the cannula, to insert it and hold it within the punctum to generate a seal. To allow control of the irrigation, the system may therefore include a switch in the vicinity of the cannula for convenient use by the operator; such a switch may be provided in the short tubular element and designed to be operated by the fingers holding the short tubular element without causing movement of the tip of the cannula.

Such a switch may be arranged to initiate operation of the flow-generating means; it may also open a valve to allow flow to occur; it may additionally activate the pressure sensor.

Under some circumstances, for example when the patient is unable to sit at the microscope or when the system is being used in an operating theatre, it will be necessary to ensure it can also be used hand-held. To achieve this, the system may be used without the connecting flexible tubing. The short tubular element is attached directly to the tip of the syringe and the irrigation is again controlled by the switch component of the short tubular element. Advantageously, the syringe driver unit can be designed to be capable of being held like a pen, the optimum position to achieve the stability needed for safe positioning of the cannula, thereby avoiding the inherent difficulties of holding a syringe carefully in position whilst simultaneously pressing the plunger. To assist in identifying the punctum and checking for fluid leakage the syringe driver unit or the short tubular element can incorporate a light directed at the tip of the cannula.

SPECIFIC DESCRIPTION

The invention will now be further and more particularly described, by way of example only, and with reference to the accompanying drawings, in which.

Figure 1:
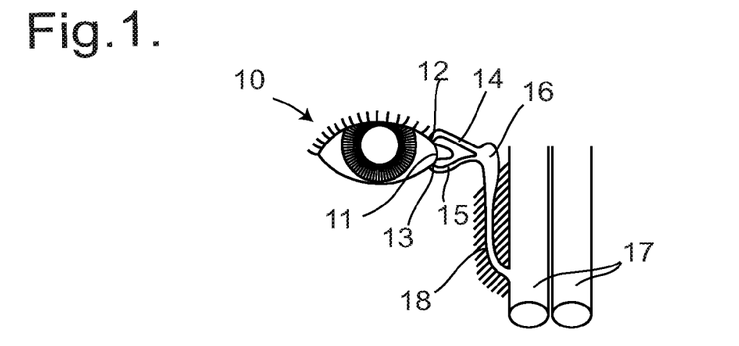
FIG. 1 shows a schematic diagram of the anatomy of a normal and healthy tear duct system.

Referring to FIG. 1, in healthy individuals, tear fluid (that is "lacrimal" fluid) is normally supplied continuously to their eyes 10 (only one is shown) from lacrimal glands. The lacrimal fluid subsequently washes the cornea and conjunctival components of the eye 10. Under healthy conditions, excess lacrimal fluid that cannot be retained by the eye and conjunctiva tends to be drained from the inner-canthus 11, at the corner of the eye, to the nasal passages 17. The fluid passes through a network of passages, starting at puncta 12, 13 which are at the centre of small papillae adjacent to the inner-canthus 11, at the margin of the eyelid. The puncta 12, 13 communicate via canaliculi 14, 15 with the lacrimal sac 16, and the tear fluid then drains through the nasolacrimal duct 18 into the nasal passage 17.

If there is a partial or total blockage of one or more of the drainage channels 14, 15, 16, 18, excess lacrimal fluid can no longer drain away in the usual fashion. Such a blockage may result from congenital anomalies, accidents, inflammation, and so forth, and will tend to cause the eye 10 to continuously brim over with tears, with concomitant discomfort to the individual, and with a potential risk of infection. Surgical treatment can correct this problem, but it is desirable to be able to check accurately the degree of blockage.

Figure 2:
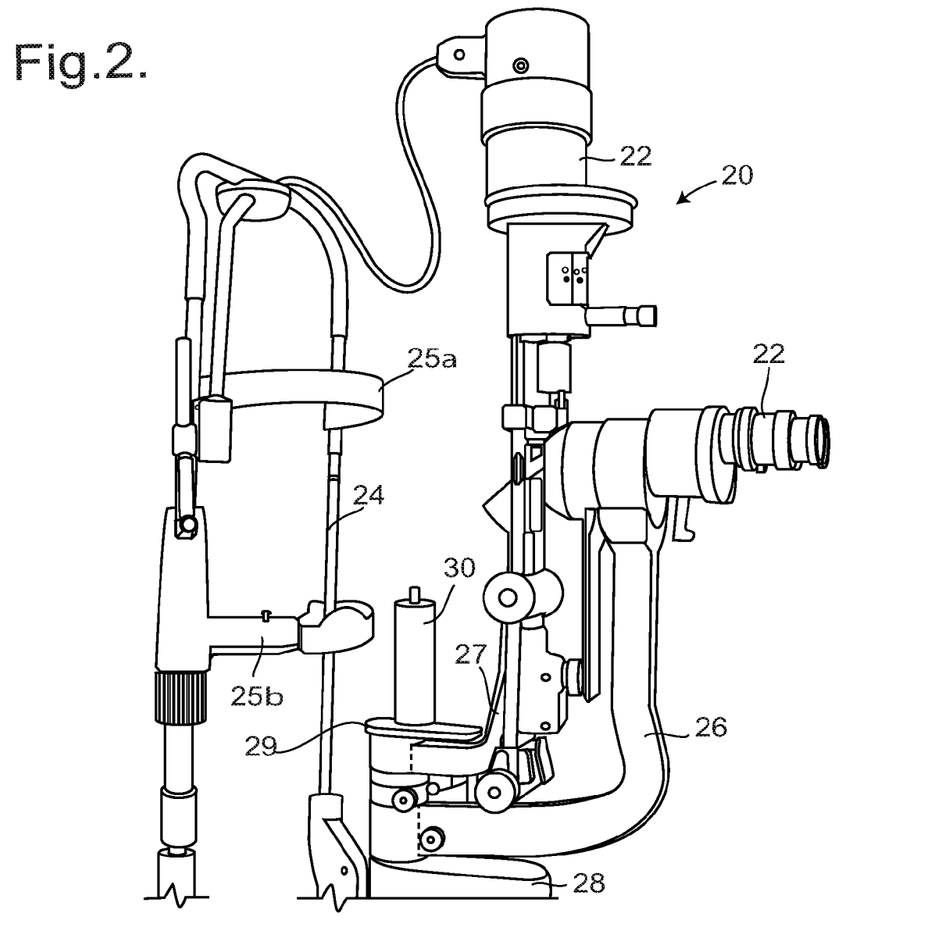
FIG. 2 shows a perspective view of an ophthalmic microscope system for use with an irrigation system.

Referring now to FIG. 2 there is shown an ophthalmic microscope system 20. This consists of an illumination system 22 including a short focus projector to project an image of an illuminated slit onto a patient's eye. The eye is observed through a binocular microscope 23. In normal use the focal position of the microscope 23 is at the same position as the focal position of the illumination system 22. In front of the microscope 23 is a support frame 24 with a curved rest 25a for a patient's forehead, and a chin rest 25b for the patient's chin. In use the patient places his head resting against the curved rest 25a and the chin rest 25b; the height of the chin rest 25b can be adjusted so that the patient's eyes are at the level of the microscope 23. Hence the surgeon can view the patient's eye through the microscope 23 and can ensure that the eye is satisfactorily illuminated. The microscope 23 is supported on an L-shaped bracket 26, and the illumination system 22 is supported on a shorter L-shaped bracket 27, both the L-shaped brackets 26 and 27 being mounted on a support 28 and being rotatable about a vertical axis. This enables the surgeon to adjust the relative orientations of the illumination and of the microscope 23. Immediately above the lower portion of the L-shaped bracket 27 is a plate or platform 29 onto which may be mounted an irrigation system 30 of the invention.

Figure 3:
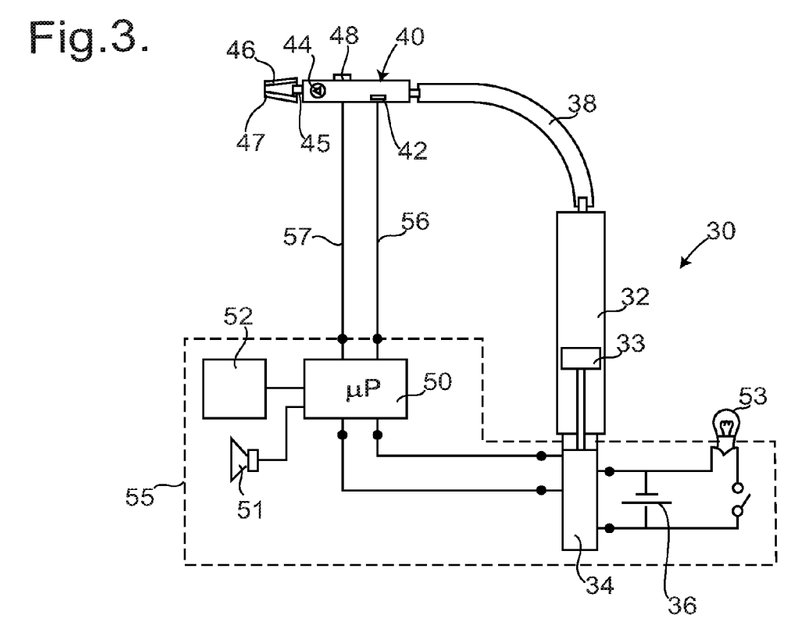
FIG. 3 shows a schematic diagram of an irrigation system of the invention.

Referring now to FIG. 3, an irrigation system 30 of the invention comprises a syringe 32 with a plunger 33. The plunger 33 can be driven by a linear actuator 34 which is powered by a battery 36. The liquid outlet of the syringe 32 is connected by a flexible tube 38 to a transducer unit 40. The transducer module 40 defines a flow channel within which is a pressure sensor 42 and a one-way valve 44 adjacent to an outlet 45. The outlet 45 is connected to a cannula 46 which, in this example, tapers to a tip 47. The transducer module 40 also includes a push-button switch 48. In a modification, the one-way valve 44 is omitted.

The irrigation system 30 also includes a microprocessor 50 connected to a display module 51 and to a loudspeaker 52. The push-button switch 48 provides on and off signals for operation of the irrigation system 30, and these are provided to the microprocessor 50, through a wire 57. The microprocessor 50 is also provided with pressure-indicating signals from the pressure sensor 42, through a wire 56, and is provided with flow-rate-indicating signals from the linear actuator 34. The microprocessor 50 provides control signals to actuate the linear actuator 34. In a modification, the microprocessor 50 may be connected to a light display instead of, or in addition to, the loudspeaker 52. (The electrical connections are shown schematically.)

If the surgeon (or other medical professional) presses the push-button switch 48 to provide an "on" signal, the microprocessor 50 initiates movement of the linear actuator 34. The microprocessor 50 monitors both the flow rate and the fluid pressure. In a first mode of operation the pressure rises to a preset value P1, the microprocessor 50 then controls the linear actuator 34 to maintain the pressure at that value P1, and the flow rate F1 is measured for that preset value of pressure. The microprocessor can consequently calculate the resistance as R1=P1/F1, and the value of this resistance R1 is displayed on the display module 51.

In an alternative mode of operation, the flow rate and pressure gradually increase until a preset flow rate F2 is obtained, the microprocessor 50 then controls the linear actuator 34 to maintain the flow rate at this value F2, and the corresponding pressure P2 is then measured. The microprocessor can consequently calculate the resistance as R2=P2/F2, and the value of resistance R2 can be displayed on the display module 51. When operating in this mode the microprocessor 50 must also monitor the pressure, to ensure that the pressure does not exceed a threshold P3 at which the patient may experience pain or damage to the tear duct.

In another alternative mode of operation, the flow rate is not measured. Instead the flow is set to a predetermined value, for example by supplying a preset voltage to the linear actuator 34. Without monitoring the linear actuator 34 and without measuring the flow rate, the pressure P can be measured. This pressure may be taken as indicative of the flow resistance. The medical professional can readily distinguish between normal values of flow resistance, and abnormal values. If the pressure becomes excessive, the flow may be reduced or cut off.

Considering the components of the irrigation system 30 in more detail, the syringe 32 may be a standard syringe, for example of capacity 5 ml or 10 ml. In some cases the microscope system 20 may provide sufficient space above the plate 29 that a 10 ml syringe can be used. However, with some microscopes systems 20 a filled 10 ml syringe may be too long, obstructing the view of the eye when fitted vertically on the plate 29. In a modification the syringe may extend at least partly below the plate 29, for example being inclined from the vertical. In another modification the tubing 38 is connected to the syringe 32 through a 90° connector, reducing the overall height. The tube 38 must be sufficiently long to connect the outlet of the syringe 32 to the transducer unit 40, with the cannula 46 able to reach the punctum 12 or 13 when the patient is positioned adjacent to the curved rest 25a and the chin rest 25b; it must be flexible but non-kinking. The tube 38 would typically be of silicone tubing. If the irrigation system 30 is to be used when hand-held, the tube 38 may be omitted, the transducer unit 40 being attached directly to the end of the syringe 32.

The cannula 46 needs to be able to seal at the punctum 12 or 13; to be short (to allow easy positioning in the narrow confines around the ophthalmic microscope system 20); to have the maximum possible lumen diameter (to ensure resistance to flow is largely due to the tear duct rather than the cannula 46); to have a short length of narrow diameter (to minimise pressure drop within the cannula 46); and to have the minimum possible outside diameter (to minimise or avoid the need for dilation of the punctum 12 or 13 to allow insertion, avoiding the need for an additional step with patient discomfort and/or risk of damage to the punctum 12 or 13), implying a thin wall. Consequently the cannula 46 preferably has a broad diameter lumen tapering smoothly to the narrower tip 47 of external diameter no more than 2 mm, for example approximately 0.6 mm, with a constant wall thickness throughout, and a total length of approximately 5-10 mm. Alternative designs are possible, for example the provision of a cone or ball at the outer surface towards the tip 47 of the cannula 46, to help it seal to the punctum 12 or 13. Other designs of cannula are described below in relation to FIGS. 5a to c. The cannula would typically be of stainless steel.

Preferably the tip 47 is sufficiently narrow that no preliminary dilation of the punctum 12 or 13 is required.

The switch 48 may be activated, either fully on or fully off, on whilst finger pressure applied, off when pressure released. The switch 48 may also constitute a valve which, when it is in the "on" position opens the passage to fluid flow; as described above its major role is to provide a signal to the microprocessor 50 to initiate flow of liquid.

The transducer module 40 includes the pressure sensor 42, which may for example use a piezo-electric transducer, which must be of appropriate sensitivity to provide continuous readouts within the anticipated range of pressures. The pressure sensor 42 may be directly exposed to the lumen within the transducer module 40 and so to the liquid flowing through it. As shown in FIG. 3, the cannula 46 is attached to the distal end of the transducer module 40, while the flexible tube 38 is attached to the proximal end (when being used in conjunction with the ophthalmic microscope system 20). The transducer module 40 must be sufficiently small that it can be easily held in the surgeon's hand, and manipulated in the restricted space between the microscope 22 and the patient's eye, and the switch 48 must be sufficiently sensitive that it can be activated without causing movement of the tip 47 engaged in the punctum 12 or 13. Clearly the transducer module 40 must not restrict the surgeon's ability to place the tip 47 into the punctum 12 or 13. Typically the transducer module 40 would be of a length between 10 mm and 100 mm, for example 15 mm, 20 mm or 25 mm.

The mechanism to activate the plunger 33 may be a linear actuator 34 as described above, acting directly as a syringe driver, but other systems to generate liquid flow are possible. For example an electric motor may drive liquid from a reservoir using a pump. Where a syringe 32 with a plunger 33 is used, a screw thread may propel a bracket arranged to move the plunger 33. The mechanism may be powered by a battery 36, which may be provided with a recharging circuit (not shown) and means to warn when recharging is required; while as an alternative the irrigation system 30 may instead be powered from the mains. The actuator 34 may include other sensors, such as a motor overload detector. The sensing of flow rate may be based on the movement of the plunger 33, or on the speed of the actuator 34, for example using optical sensors, or from measurements on the motor itself, such as armature voltage.

The linear actuator 34, the battery 36, the microprocessor 50 and the display module 52 are housed within a casing 55 (indicated in broken lines in FIG. 3), which would typically be of a moulded thermoplastic. Electric wires 56 and 57 from the pressure sensor 42 and the switch 48 may therefore be in the form of a flexible lead which connects to the casing 55 with a plug. The casing 55 incorporates means to mount the syringe 32, and from which the syringe 32 can be removed. The casing 55 may be ergonomically shaped for hand-held operation, preferably with a pen-like grip, and may include a light source 53 to illuminate the punctum 12 or 13 during hand-held operation. In addition the irrigation system 30 includes a bracket for connecting the casing 55 on to the plate 29 of the ophthalmic microscope system 20 in the orientation shown in FIG. 3, preferably with the outlet of the syringe 32 at the top.

Figure 4A:
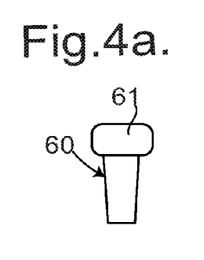
FIGS. 4a to 4e show different punctual occluders of the invention.
Figure 4B:
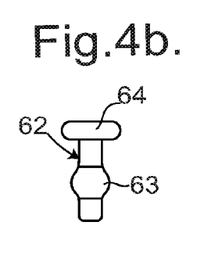

The irrigation system 30 also includes a punctal occluder, that is to say a clip or plug that can be applied to one punctum 12 or 13 that simply, reliably, safely, painlessly and reversibly closes off the punctum 12 or 13, before liquid is injected into the other punctum 12 or 13. Referring to FIG. 4a the punctal occluder may be a tapered plug 60 with a larger head 61 at one end; the operator would hold the head 61 and insert the tapered plug 60 into the punctum 12 or 13 to prevent any liquid flow. As shown in FIG. 4b the punctal occluder may be a plug 62 with a narrow shaft with a bulbous portion 63, and with a larger head 64 at one end; the operator would hold the head 64, and insert the plug 62 until the bulbous portion 63 had blocked the punctum 12 or 13.

Figure 4C:
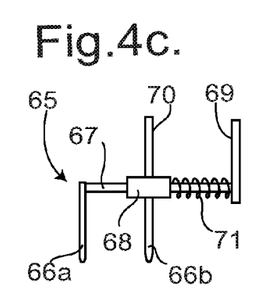
Figure 4D:
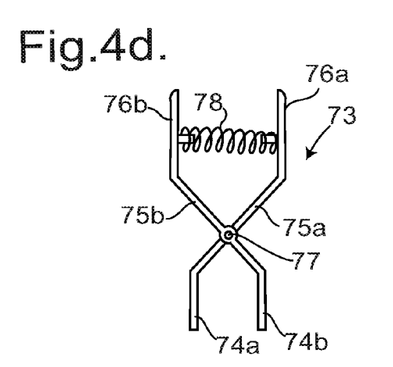
Figure 4E:
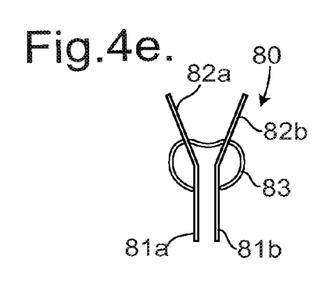

As an alternative and more convenient approach to plugging the punctum, the punctum or adjacent canaliculus may be closed by externally applied pressure with a clip. This may be achieved by squeezing the canaliculus 14 or 15 between two opposed jaws. The jaws may be brought together using a screw thread; but preferably such jaws are mounted resiliently. This squeezing approach may be applied directly to the punctum 12 or 13 itself. Suitable occluders are shown in FIGS. 4c, 4d and 4e. In each case the jaws would typically be of a plastic material, whereas the spring would be of a metal such as stainless steel.

As shown in FIG. 4c a punctal occluder 65 may comprise a pair of opposed jaws 66a and 66b, one attached to the end of a rod 67 and the other projecting from a sleeve 68 that can slide along the rod 67. To the opposite end of the rod 67 is fixed a projecting finger-plate 69, and a second finger-plate 70 projects from the sleeve 68; a compression spring 71 urges the sleeve 68 along the rod 67 so as to urge the jaws 66a and 66b together. The operator would squeeze the finger-plates 69 and 70 together to separate the jaws 66a and 66b; place the jaws 66a and 66b inside and outside the eyelid on the medial side of the punctum 12 or 13; and then release the finger-plates 69 and 70, so the jaws 66a and 66b squeeze the corresponding canaliculus 14 or 15 closed.

Alternatively, as shown in FIG. 4d, a punctal occluder 73 may comprise a pair of opposed jaws 74a and 74b at the ends of two pivoted arms 75a and 75b which define finger plates 76a and 76b at their other ends, linked by a pivot pin 77, and with a compression spring 78 arranged to urge the finger plates 76a and 76b apart. This occluder 73 resembles a small-scale pair of spring-loaded tongs or scissors. It is used in a similar way to the occluder 65, in that the operator would squeeze the finger plates 76a and 76b together; place the jaws 74a and 74b inside and outside the eyelid on the medial side of the punctum 12 or 13; and then release the finger-plates 76a and 76b so the jaws 74a and 74b squeeze the corresponding canaliculus 14 or 15 closed.

Alternatively, as shown in FIG. 4e, a punctal occluder 80 may comprise a pair of opposed jaws 81a and 81b integral with finger plates 82a and 82b, held together by a part-cylindrical spring 83. This occluder 80 resembles a small-scale bulldog clip. It is used in a similar way to the occluders 65 and 73 described above.

Method of Use

The irrigation system 30 is prepared by filling the syringe 32 with a suitable liquid, typically water or saline. The syringe 32 is then fixed on to the casing 55, and the casing 55 mounted on the plate 29; the tube 38 and the transducer module 40 are connected to the syringe 32; the wires 56 and 57 from the transducer module 40 are plugged into the casing 55; and the cannula 46 is connected to the end of the transducer module 40.

The casing 55 may also be provided with an on/off switch, and a priming/calibration button (not shown). In this case the switch would be switched on, and the system primed and checked. This ensures air is expelled from the system and that the pressure sensor 42 is responding as anticipated. When the priming function is activated, the operator may for example be allowed a few seconds to press the switch 48 to the "on" position. Fluid flow is then initiated at a defined rate or rates, and the output of the pressure sensor 42 is monitored; the pressure rises due to the small diameter of the tip 47. If the pressure or pressures reach values within required limits, the priming and testing is considered satisfactory. This may be indicated by a sound from the speaker 52 (or by a coloured light). The resistance so recorded represents the inherent resistance of the system when not irrigating the tear duct and the system can therefore be calibrated such that this level of resistance represents free flow.

The operator then uses a punctual occluder to block one punctum of the patient's eye 10, for example the upper punctum 12. While viewing the eye through the microscope 22, the operator with one hand holds the patient's eyelid, and with the other hand holds the transducer module 40, and carefully engages the cannula tip 47 with the other punctum, in this case the lower punctum 13. The operator can then initiate fluid flow by holding down the switch 48, which actuates the linear actuator 34 as described above.

In a suitable mode of operation, the microprocessor 50 initially assumes that the resistance will have a normal value, and initiates liquid flow at a preset rate. The pressure is monitored using the signals from the sensor 42, and if the pressure is too low the fluid flow is increased, while if the pressure is too high the fluid flow is reduced. Hence the microprocessor 50, using the feedback of pressure values, brings the pressure to a value in a pre-determined range and the fluid flow to a steady state. Damping circuitry in the microprocessor 50 is arranged to avoid wide swings or overshoots, so as to rapidly reach a steady state and thereby minimise the amount of fluid irrigation required. This ensures a more comfortable test for the patient and less need to replenish the fluid in the syringe. If the values are steady for a sufficient time, preferably at least 1 second and more preferably at least 2 seconds, then the values of pressure and flow are measured, and the microprocessor can deduce the resistance of the patient's tear duct (between the punctum, in this case the lower punctum 13, and the nasal channel 17).

The flow rate is typically in the range from 5 to 10 ml/min; and the injection pressure might for example be in the range from 10 to 20 cm water, that is 1 to 2 kPa. For a normal, healthy person the resistance of the tear duct is around 6.7 kPa·s/ml, although there can be a wide variation between individuals, typically between about 4.4 kPa·s/ml and 9.0 kPa·s/ml. The feedback control system however ensures that the irrigation system 30 is able to be used safely and accurately in individuals where the resistance is normal, significantly greater than normal, or where the drainage system is completely obstructed.

Thus if the microprocessor 50 detects that the pressure has exceeded a threshold value, it reduces the flow, or switches off fluid flow completely to avoid discomfort to the patient or damage to the tear duct or to the linear actuator 34.

If, as mentioned above, a steady state is achieved for an adequate duration, then one or more measurements of flow rate and pressure are recorded by the microprocessor 50. The microprocessor 50 may then provide an audible signal through the loudspeaker 52 to indicate that the test has been successful, and switches off the linear actuator 34. The microprocessor 50 then calculates and averages results for resistance (Resistance=Pressure/Flow), and displays the result on the display unit 51, optionally in comparison with the corresponding figures for a healthy individual.

Safety in use is ensured firstly by ceasing actuation of the linear actuator 34 if the pressure sensor within the transducer module 40 rises above a pre-set limit or threshold. In addition, the provision of a motor overload detector on the linear actuator 34 guards against the flexible tube 38 being blocked, for example by kinking, as this would provide a high resistance to fluid flow without generating high pressure in the transducer module 40.

The irrigation system 30 provides advantages both for the surgeon and for the patient. For the surgeon, the system 30 provides objective data on lacrimal resistance, and the measurements are made under conditions that are closer to the natural physiological state. The measurements are easier, as they can be made using the microscope to provide excellent visibility for inserting the occluder and for inserting the tip 47 of the cannula 46, and for checking for any leaks. The measurements are also easier when using the irrigation system 30 hand-held, without the flexible tube 38, as the system is lightweight, providing an ergonomic hand position, and a comparatively short distance from the hand to the tip 47 of the cannula 46. From the patient's perspective the measurements are safer, with less risk of damage to the canaliculi either during insertion or arising from excess pressure; and the measurements are less uncomfortable, as the flow rate and quantity of liquid is less.

The one-way valve 44 minimises the risk of contamination reaching the flexible tube 38, or the syringe 32 if the flexible tube 38 is not provided. Consequently, after use the transducer module 40 and the cannula 46 would typically be disposable, whereas the other components can be reused without risk of transferring contamination. Alternatively, where no one-way valve 44 is provided, then the syringe 32, flexible tube 38, transducer module 40 and cannula 46 may all be disposable.

It will be appreciated that the irrigation system 30 described above may be modified in various ways. For example the cannula 46 may be replaced by a differently-shaped cannula.

Figure 5A:
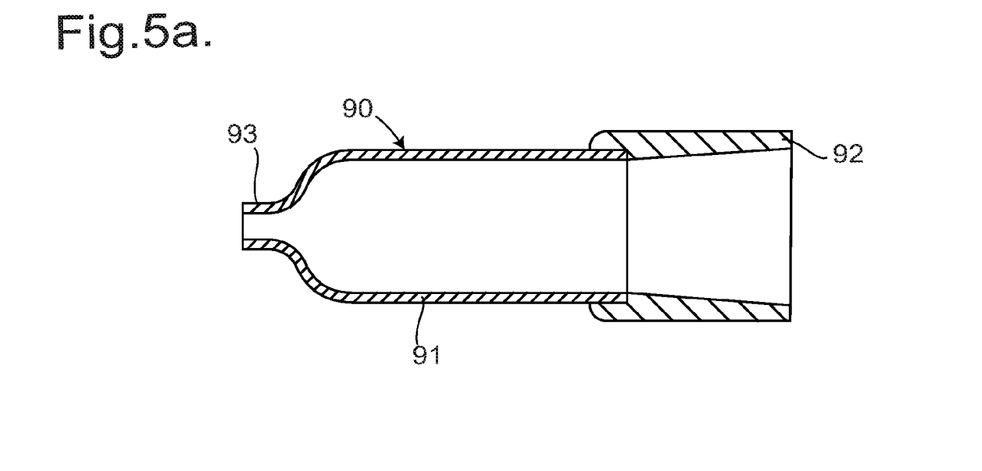
FIGS. 5a to 5c show sectional views of alternative cannulas for the system of FIG. 3.

Referring to FIG. 5a, an alternative cannula 90 comprises a thin-walled tube 91 provided with a hub 92 at one end, for connection to the outlet 45 of the transducer module 40, and at the other end having a smooth transition down to a short narrow tube section 93. This is used as described above, with the short section 93 being inserted into the punctum 12 or 13.

Figure 5B:
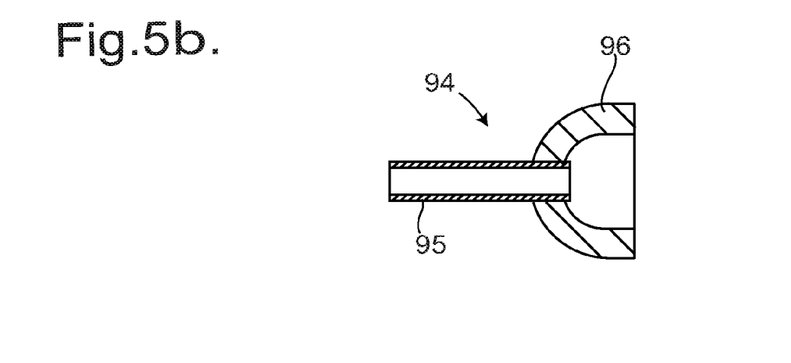

As shown in FIG. 5b, another alternative cannula 94 comprises a stainless steel tube 95 of uniform outside diameter e.g 0.64 mm, and of length for example 4 or 5 mm, inserted into a hub 96 that provides a rounded surface towards the tip of the cannula 94. The internal diameter may be around 0.54 mm for a 0.05 mm wall thickness. This size generally does not need dilation before insertion, and the hub 96 may provide the seal to the punctum 12 or 13. Alternatively the tube 95 might have an external diameter 0.57 mm, again with a wall thickness of 0.05 mm. Although the tube 95 is shown as straight, it might instead have a slight curve along its length.

Figure 5C:
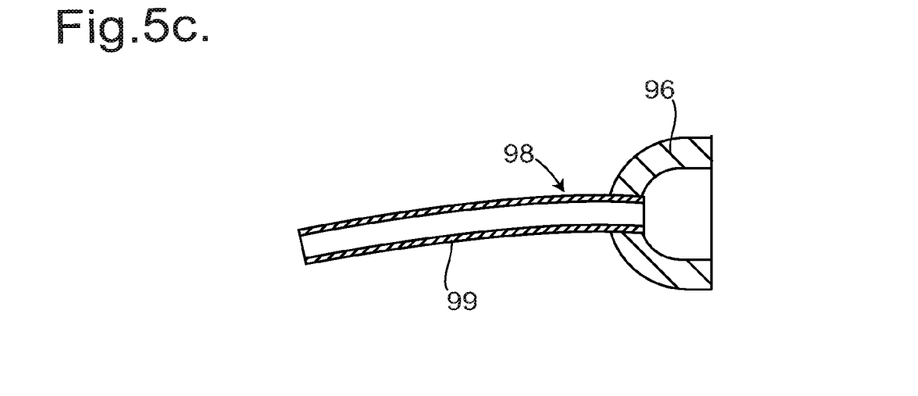

Referring to FIG. 5c, there is shown a cannula 98 which is a modification of the cannula 94, differing in having a longer tube 99 which in this example is slightly curved. This may be around 9-10 mm long, so it would be possible to pass it along the canaliculus 14 or 15 and into the lacrimal sac 16, with the hub 96 sealing at the punctum 12 or 13. This can provide an advantage. Tear duct narrowing is known to most commonly occur in the lacrimal duct 18, and when measuring lacrimal resistance what one really would like to know is the resistance of this part. Irrigating from the punctum 12 or 13, using for example cannula 94, would indicate the total resistance beyond this point; so to identify narrowing of the lacrimal duct 18 one has to assume the canaliculus 14 or 15 is normal. The cannula 98 enables the flow resistance of the lacrimal duct 18 to be measured more precisely, and by comparison with measurements using for example the cannula 94, an objective measurement can be obtained indicating where the narrowing of the tear duct occurs.

The transducer module 40 may also be modified. For example it may include a mechanical valve to prevent liquid flow, this being actuated by pressing the push-button switch 48 that also provides the electrical signal in the wire 57.

The invention claimed is:

1. A system for measuring flow properties of a tear duct, to ascertain flow resistance of the tear duct, the system comprising:
    syringe with a plunger to generate a flow of liquid, communicating with a cannula to supply liquid into a punctum of an eye to irrigate the tear duct, the liquid being supplied into the punctum at a flow rate, the cannula defining a tip, and being able to seal to the punctum;
    a linear actuator to actuate the plunger of the syringe, to generate the flow of liquid;
    a pressure sensor to monitor the pressure of the liquid supplied to the punctum;
    a monitoring circuit to which signals from the pressure sensor are provided, arranged to provide an indication of the flow resistance from those signals; and
    a feedback circuit to which signals from the pressure sensor are provided, and which provides signals to the linear actuator to control the linear actuator in accordance with the signals from the pressure sensor, to change the flow rate from the syringe either to maintain a preset liquid pressure, or to ensure that the liquid pressure does not exceed a preset threshold;
    wherein the syringe communicates with the cannula through one or more components that define a flow path, the flow path being defined at least in part by a short, rigid tubular element to which the cannula is attached; and the system includes a switch in the vicinity of the cannula for convenient use by an operator, the switch enabling activation of the linear actuator and so operation of the syringe;
    and the syringe and the linear actuator are adapted to be mounted on a microscope; and the flow path is defined at least in part by a flexible tube; the flexible tube being sufficiently long to enable an operator to insert the cannula into a patient's punctum while the operator views the patient's eye through the microscope, with the syringe and the linear actuator mounted on the microscope.

2. A system as claimed in claim 1, also comprising means to monitor the flow rate of the liquid supplied to the punctum, and to supply signals representing the flow rate to the monitoring circuit, so the monitoring circuit can determine the flow resistance.

3. A system as claimed in claim 1, for use where the eye has a normal tear duct system with two puncta, the system also comprising means to occlude flow through the other punctum of the eye, the occluding means comprising a clip to compress a punctum or adjacent canaliculus between two opposed jaws.

4. A system as claimed in claim 2, wherein the flow rate is monitored by monitoring movement of the syringe plunger, or by monitoring the linear actuator.

5. A system as claimed in claim 1, wherein the pressure sensor is within the short tubular element.

6. A system as claimed in claim 1, wherein the short tubular element also comprises the switch.

7. A system as claimed in claim 1, wherein the short tubular element also comprises a one-way valve.

8. A system as claimed in claim 1, wherein the tubular element also comprises a source of light directed at the tip of the cannula, to assist the user in identifying the punctum, and to check for liquid leakage during operation.

9. A system as claimed in claim 1, also comprising
    a motor overload detector to detect any overload of the linear actuator.

10. A system as claimed in claim 1, wherein the flexible tube is disconnectable, and the syringe is connectable directly to the tubular element, so the system can be used hand-held.

11. A system for measuring flow properties of a tear duct, to ascertain flow resistance of the tear duct; the system comprising:
    a syringe with a plunger to generate a flow of liquid, communicating with a cannula to supply liquid into a punctum of an eye to irrigate the tear duct, the liquid being supplied into the punctum at a flow rate; the cannula defining a tip; and being able to seal to the punctum;
    a linear actuator to actuate the plunger of the syringe, to generate the flow of liquid;
    a pressure sensor to monitor the pressure of the liquid supplied to the punctum;
    a monitoring circuit to which signals from the pressure sensor are provided, arranged to provide an indication of the flow resistance from those signals;
    a feedback circuit to which signals from the pressure sensor are provided, and which provides signals to the linear actuator to control the linear actuator in accordance with the signals from the pressure sensor, to change the flow rate from the syringe either to maintain a preset liquid pressure, or to ensure that the liquid pressure does not exceed a preset threshold; and
    occluding means to occlude flow through a second punctum of the eye, the occluding means comprising a clip to compress a punctum or adjacent canaliculus between two opposed jaws, the jaws configured to be placed respectively inside and outside an eyelid of the eye, so as to compress a portion of the eyelid containing the second punctum or an adjacent canaliculus connected to the second punctum;

wherein the syringe communicates with the cannula through one or more components that define a flow path, the flow path being defined at least in part by a short, rigid tubular element to which the cannula is attached; and the system includes a switch in the vicinity of the cannula for convenient use by an operator, the switch enabling activation of the linear actuator and so operation of the syringe; and wherein the system is portable and battery powered, so that the system may be operated hand-held.

12. A system as claimed in claim 11, also comprising means to monitor the flow rate of the liquid supplied to the punctum, and to supply signals representing the flow rate to the monitoring circuit, so the monitoring circuit can determine the flow resistance.

13. A system as claimed in claim 12, wherein the flow rate is monitored by monitoring movement of the syringe plunger, or by monitoring the linear actuator.

14. A system as claimed in claim 11, wherein the pressure sensor is within the short tubular element.

15. A system as claimed in claim 11, wherein the short tubular element also comprises the switch.

16. A system as claimed in claim 11, wherein the short tubular element also comprises a one-way valve.

17. A system as claimed in claim 11, wherein the system also comprises a source of light directed at the tip of the cannula, to assist the user in identifying the punctum, and to check for liquid leakage during operation.

18. A system as claimed in claim 11, also comprising a motor overload detector to detect any overload of the linear actuator.

19. A system for measuring flow properties of a tear duct, to ascertain flow resistance of the tear duct, the system comprising:
    a liquid reservoir, communicating with a cannula to supply liquid into a punctum of an eye to irrigate the tear duct, the cannula defining a tip, and being able to seal to the punctum;
    a pump to generate a flow of liquid from the liquid reservoir to the cannula, the liquid being supplied into the punctum at a flow rate,
    a pressure sensor to monitor the pressure of the liquid supplied to the punctum;
    a monitoring circuit to which signals from the pressure sensor are provided, arranged to provide an indication of the flow resistance from those signals; and
    a feedback circuit to which signals from the pressure sensor are provided, and which provides signals to the pump to control the pump in accordance with the signals from the pressure sensor, to change the flow rate of liquid from the pump either to maintain a preset liquid pressure, or to ensure that the liquid pressure does not exceed a preset threshold;
    wherein the liquid reservoir communicates with the cannula through one or more components that define a flow path, the flow path being defined at least in part by a short, rigid tubular element to which the cannula is attached; and the system includes a switch in the vicinity of the cannula for convenient use by an operator, the switch enabling activation of the pump and so initiation of the liquid flow;
    and wherein the liquid reservoir and the pump are adapted to be mounted on a microscope; and the flow path is defined at least in part by a flexible tube; the flexible tube being sufficiently long to enable an operator to insert the cannula into a patient's punctum while the operator views the patient's eye through the microscope, with the liquid reservoir and pump mounted on the microscope.

20. A system as claimed in claim 19, also comprising means to monitor the flow rate of the liquid supplied to the punctum, and to supply signals representing the flow rate to the monitoring circuit, so the monitoring circuit can determine the flow resistance.

21. A system as claimed in claim 19, for use where the eye has a normal tear duct system with two puncta, the system also comprising means to occlude flow through the other punctum of the eye, the occluding means comprising a clip to compress a punctum or adjacent canaliculus between two opposed jaws.

22. A system as claimed in claim 19, wherein the pressure sensor is within the short tubular element.

23. A system as claimed in claim 19, wherein the short tubular element also comprises the switch.

24. A system as claimed in claim 19, wherein the short tubular element also comprises a one-way valve.

25. A system as claimed in claim 19, wherein the tubular element also comprises a source of light directed at the tip of the cannula, to assist the user in identifying the punctum, and to check for liquid leakage during operation.

26. A system as claimed in claim 19, also comprising a motor overload detector to detect any overload of the pump.

27. A system as claimed in claim 19, wherein the flexible tube is disconnectable, and the pump is connectable directly to the tubular element, so the system can be used hand-held.

28. A system for measuring flow properties of a tear duct, to ascertain flow resistance of the tear duct, the system comprising:
    a liquid reservoir, communicating with a cannula to supply liquid into a punctum of an eye to irrigate the tear duct, the cannula defining a tip, and being able to seal to the punctum;
    a pump to generate a flow of liquid from the liquid reservoir to the cannula, the liquid being supplied into the punctum at a flow rate,
    a pressure sensor to monitor the pressure of the liquid supplied to the punctum;
    a monitoring circuit to which signals from the pressure sensor are provided, arranged to provide an indication of the flow resistance from those signals;
    a feedback circuit to which signals from the pressure sensor are provided, and which provides signals to the pump to control the pump in accordance with the signals from the pressure sensor, to change the flow rate of liquid from the pump either to maintain a preset liquid pressure, or to ensure that the liquid pressure does not exceed a preset threshold; and
    occluding means to occlude flow through a second punctum of the eye, the occluding means comprising a clip to compress a punctum or adjacent canaliculus between two opposed jaws, the jaws configured to be placed respectively inside and outside an eyelid of the eye, so as to compress a portion of the eyelid containing the second punctum or an adjacent canaliculus connected to the second punctum;
    wherein the liquid reservoir communicates with the cannula through one or more components that define a flow path, the flow path being defined at least in part by a short, rigid tubular element to which the cannula is attached; and the system includes a switch in the vicinity of the cannula for convenient use by an operator, the switch enabling activation of the pump and so initiation of the liquid flow;

and wherein the system is portable and battery powered, so that the system may be operated hand-held.

29. A system as claimed in claim 28, also comprising means to monitor the flow rate of the liquid supplied to the punctum, and to supply signals representing the flow rate to the monitoring circuit, so the monitoring circuit can determine the flow resistance.

30. A system as claimed in claim 28, wherein the pressure sensor is within the short tubular element.

31. A system as claimed in claim 28, wherein the short tubular element also comprises the switch.

32. A system as claimed in claim 28, wherein the short tubular element also comprises a one-way valve.

33. A system as claimed in claim 28, wherein the tubular element also comprises a source of light directed at the tip of the cannula, to assist the user in identifying the punctum, and to check for liquid leakage during operation.

34. A system as claimed in claim 28, also comprising a motor overload detector to detect any overload of the pump.

* * * * *